(12) United States Patent
Loeb et al.

(10) Patent No.: US 9,743,491 B2
(45) Date of Patent: Aug. 22, 2017

(54) SYSTEM AND METHOD UTILIZING BIO-ALGORITHMS FOR LIGHT FIXTURE NETWORKS

(71) Applicants: Michael R. Loeb, New York, NY (US); Jason Slosberg, Montclair, NJ (US); Andrew Bein, Riverside, CT (US); Alvin Kopel, Westminster, CO (US); Edward J. McCabe, New York, NY (US); John F. Rovegno, Stamford, CT (US)

(72) Inventors: Michael R. Loeb, New York, NY (US); Jason Slosberg, Montclair, NJ (US); Andrew Bein, Riverside, CT (US); Alvin Kopel, Westminster, CO (US); Edward J. McCabe, New York, NY (US); John F. Rovegno, Stamford, CT (US)

(73) Assignee: LINKBEE, LLC, New York, NY (US)

( * ) Notice: Subject to any disclaimer, the term of this patent is extended or adjusted under 35 U.S.C. 154(b) by 0 days.

(21) Appl. No.: 14/747,694

(22) Filed: Jun. 23, 2015

(65) Prior Publication Data
US 2016/0381763 A1 Dec. 29, 2016

(51) Int. Cl.
*H05B 37/02* (2006.01)
*A61N 5/06* (2006.01)

(52) U.S. Cl.
CPC ....... *H05B 37/0227* (2013.01); *A61N 5/0618* (2013.01); *H05B 37/0272* (2013.01); *A61N 2005/0626* (2013.01); *A61N 2005/0651* (2013.01)

(58) Field of Classification Search
None
See application file for complete search history.

(56) References Cited

U.S. PATENT DOCUMENTS

| | | | |
|---|---|---|---|
| 7,207,938 B2 * | 4/2007 | Hursh | A61B 5/4809 128/920 |
| 8,847,508 B2 * | 9/2014 | Huang | H05B 37/0227 315/291 |
| 2012/0209358 A1 * | 8/2012 | Feng | A61M 21/00 607/90 |
| 2014/0052220 A1 * | 2/2014 | Pedersen | A61N 5/0618 607/88 |
| 2015/0048742 A1 * | 2/2015 | Wingren | H05B 37/0218 315/152 |
| 2015/0174361 A1 * | 6/2015 | Baaijens | A61N 5/0618 315/131 |

* cited by examiner

*Primary Examiner* — Douglas W Owens
*Assistant Examiner* — James H Cho
(74) *Attorney, Agent, or Firm* — Buckley, Maschoff & Talwalkar LLC

(57) ABSTRACT

According to some embodiments, information about at least one user associated with a light fixture network, having a plurality of light fixtures each equipped with a wireless communication device, may be received. A bio-algorithm to be applied to the light fixture network may then be determined based on the information about the at least one user. An appropriate lighting parameter (e.g., a luminescence, a wattage, a color characteristic, and/or a wavelength) for at least one of the light fixtures in the light fixture network may be dynamically calculated, and it may be arranged for the at least one light fixture to operate in accordance with the dynamically calculated lighting parameter.

25 Claims, 17 Drawing Sheets

SYSTEM AND METHOD UTILIZING BIO-ALGORITHMS FOR LIGHT FIXTURE NETWORKS

FIELD OF THE INVENTION

In general, the invention relates to a computerized system and method utilizing bio-algorithms for light fixture networks.

BACKGROUND OF THE INVENTION

It known that different types of light can have different biometric effects on the human body. For example, light may be used to treat the symptoms of Seasonal Affective Disorder ("SAD"). According to some theories, the effectiveness of light therapy in treating SAD may be linked to the fact that the light therapy makes up for lost sunlight exposure and resets the body's internal clock. In particular, light therapy may help reduce some symptoms of SAD, such as excessive sleepiness and fatigue. Similarly, light may be used in the treatment of non-seasonal depression, Sundown Syndrome, and other psychiatric disturbances, including major depressive disorder, bipolar disorder, and postpartum depression. As other examples, Circadian Rhythm Sleep Disorders ("CRSD"), including chronic CRSD, Delayed Sleep Phase Disorder ("DSPD"), and situational CRSD (e.g., associated with working a night shift or jet lag) may be treated with light. As a result, automated, efficient, and accurate ways to use light to improve a user's health and well-being may be desired.

SUMMARY

Therefore, there is a need in the art for ways to facilitate the use light to improve a user's health and well-being. Such measures may, according to some embodiments, receive information about at least one user associated with a light fixture network, having a plurality of light fixtures each equipped with a wireless communication device. A bio-algorithm to be applied to the light fixture network may then be determined based on the information about the at least one user. An appropriate lighting parameter (e.g., a luminescence, a wattage, a color characteristic, and/or a wavelength) for at least one of the light fixtures in the light fixture network may be dynamically calculated, and it may be arranged for the at least one light fixture to operate in accordance with the dynamically calculated lighting parameter.

Some embodiments may be associated with: means for receiving information about at least one user associated with a light fixture network having a plurality of light fixtures each equipped with a wireless communication device; means for determining, based on the information about the at least one user, a bio-algorithm to be applied to the light fixture network; means for dynamically calculating an appropriate lighting parameter for at least one of the light fixtures in the light fixture network; and means for arranging for the at least one light fixture to operate in accordance with the dynamically calculated lighting parameter.

According to another aspect, the invention relates to computerized methods for carrying out the functionalities described above. According to another aspect, the invention relates to non-transitory computer readable medium having stored therein instructions for causing a processor to carry out the functionalities described above.

DESCRIPTION OF CERTAIN ILLUSTRATIVE EMBODIMENTS

To provide an overall understanding of the invention, certain illustrative embodiments will now be described, including systems and methods to facilitate use of energy efficient light fixtures. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

Figure 1:
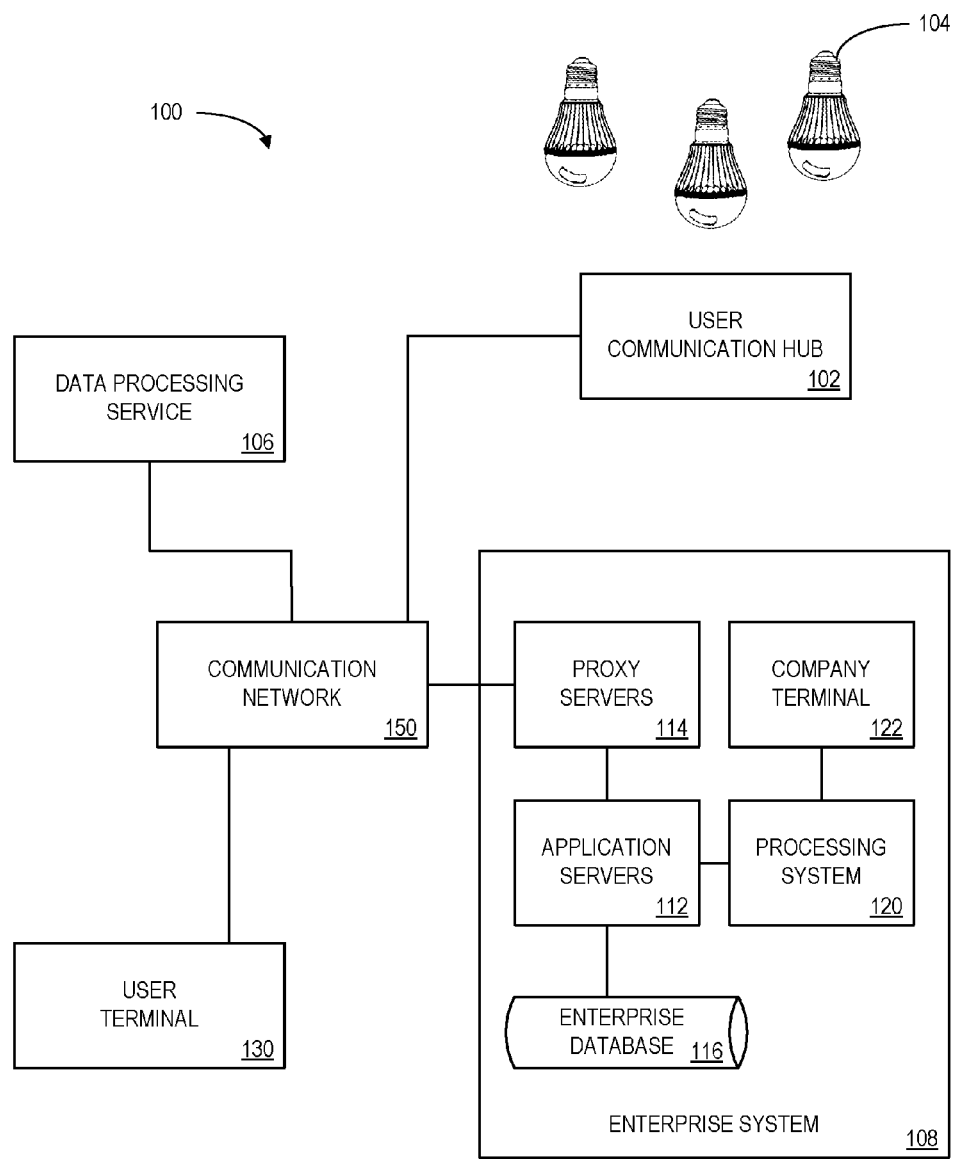
FIG. 1 is an architectural model of a system to facilitate the use of light fixtures according to an illustrative embodiment of the invention.

FIG. 1 is an architectural model of a system 100 to facilitate use of "light fixtures" 104 according to an illustrative embodiment of the invention. According to some embodiments, the light fixtures comprise energy efficient light fixtures, and, as used herein, the term "energy efficient light fixtures" might refer to, for example, an LED light fixture or any other type or source of illumination. The system 100 may, in some embodiments, collect user information and/or energy consumption data associated with operation of the energy efficient light fixtures 104.

According to some embodiments, the system includes a user communication hub 102 that controls certain lighting characteristics of the light fixtures 104. The user communication hub 102 may, for example, store information about a user and, based on the user information and one or more bio-algorithms, transmit information to adjust operation of the light fixtures 104 (e.g., adjusting the color or other characteristic of the light fixtures 104 throughout the day to help improve the user's health).

According to some embodiments, user communication hub 102 collects data about the light fixtures 104. Together, the user communication hub 102 and light fixtures 104 may comprise a network remote from an enterprise. Note that the light fixtures 104 might communicate with the communication hub 102 in any number of ways including wirelessly, via power lines, etc. The user communication hub 102 may be positioned inside a user's home, attached to the outside of the home, and/or be integrated into one or more light fixtures. As used herein, the term "home" might refer to any type of dwelling, including a standalone house, an apartment building, a co-op unit, etc. The user communication hub 102 may be in communication with an enterprise system 108 over a communication network 150. The light fixtures 104 and/or the user communication hub 102 may communicate with the enterprise system 108 though a wireless network such as a cellular network or using a wireless Internet connection. In general, the user communication hub 102 can be any computing device or plurality of computing devices in cooperation having a data collection sensor (e.g., an antenna), a processor, a memory, and a means for transmitting the collected data. The light fixtures 104 may wirelessly transmit information about user behaviors (e.g., when the fixtures 104 are turned on or are in standby mode) and/or an amount of actual energy usage. In one implementation, the user communication hub 102 is also configured to process the collected data. In some embodiments, the user communication hub 102 or other elements of the system 100 protect a user's privacy by encrypting the data, removing personal information, producing summary information, and/or taking other measures to reduce the likelihood that sensitive information is received by the enterprise or third parties.

In some embodiments, rather than sending collected data directly to the enterprise system 108, the user communication hub 102 sends collected data to a data processing service 106, which processes the data to determine a result that is then sent to the enterprise system 108. This can help protect a user's privacy, since the enterprise does not get detailed data about a user's behavior or health, but only receives summary information. Using a data processing service 106 is in some implementations also preferable to having the user communication hub 102 process data and execute bio-algorithms because it reduces the processing power needed by user communication hub 102 and because using a third party data processing service 106 may also make it more difficult for users to tamper with the data. The data processing service 106 can perform additional monitoring functions, such as functions associated with other types of sensors (e.g., home security sensors). Note that an enterprise might receive detailed reports from the third party data processing service 106, summary reports (with certain details removed), and/or supplemented information (e.g., including information from one or more public databases). According to some embodiments, a user may access data via a user terminal 130 (e.g., the user might view a current savings amount via a web page). Note that in some embodiments, a detailed record might be created recording all of the information associated with a large number of communication hubs 102, including the status of light fixtures, the number of people in various rooms, the movement of people between rooms, etc. According to some embodiments summaries of this large store of information may be generated (e.g., on a ZIP code level).

According to some embodiments, an enterprise may use energy consumption data to allocate a savings amount between a user and the enterprise. With a sufficient amount of data, the enterprise can calculate a predicted amount of usage or savings for the user based on, for example, the user's habits. The enterprise can use the savings amount for setting or adjusting a discount value to be applied to the user. In some implementations, a score or discount is determined by the enterprise and/or a third party data processing service.

In addition, the score or discount may be set by an automated process, which may be executed by the enterprise or otherwise affiliated with or in a third party arrangement with the enterprise. According to any embodiments described herein, a score might be used to determine a rebate, an energy company utility bill adjustment, and/or any other benefit that may be associated with a user.

According to some embodiments, such as the one illustrated in FIG. 1, the enterprise system 108 includes a plurality of application servers 112, a plurality of load balancing proxy servers 114, an enterprise database 116, a processing system 120, and a company terminal 122. These computing devices are connected by a local area network. Note that embodiments might be implemented using any other arrangement of computing devices, including a mesh of light fixtures, cloud storage, wide area networks, and/or a set of sensors that transmit information over one or more networks.

The application servers 112 are responsible for interacting with the user communication hub 102 and/or the data processing service 106. The data exchanged between the enterprise system 108 and user communication hub 102 and/or data processing service 106 can utilize push and pull technologies where the application servers 112 of the enterprise system 108 can act as both a server and client for pushing data to the data processing service 106 (e.g., which light fixtures 104 to control, when to stop data collection, rules for monitoring services requested by the user) and for pulling data from the data processing service 106. The application servers 112 or other servers of the enterprise system 108 can request to receive periodic data feeds from the user communication hub 102 and/or data processing service 106. The communication between the application servers 112 and the data processing service 106 can follow various known communication protocols, such as TCP/IP. Alternatively, the application servers 112 and data processing service 106 can communicate with each other wirelessly, e.g., via cellular communication, Wi-Fi, Wi-Max, or other wireless communications technologies or combination of wired or wireless channels. The load balancing proxy servers 114 operate to distribute the load among application servers 112.

The enterprise database 116 might store information about user behaviors, health, etc. For each user, the database 116 might include for example and without limitation, the following data fields: an identifier, a user subsidy amount, a date of purchase, dates of subsequent renewals, product and price of product sold, applicable automation services (for example, electronic billing, automatic electronic funds transfers, centralized user service plan selections, etc.), user information, user payment history, bio-algorithm selections, user demographic and/or health information, sensor information or derivations thereof The processing system 120 is configured for facilitating use of bio-algorithms and/or allocating an energy savings amount between a user and the enterprise. The processing system 120 may comprise multiple separate processors, such as a bio-algorithm processor, which may calculate an appropriate light characteristic value from raw or processed data from the user communication hub 102 or data processing service 106 over the communications network 150; and/or a business logic processor, which determines an appropriate savings amount for a user. An exemplary implementation of a computing device for use in the processing system 120 is discussed in greater detail in relation to FIG. 2.

The company terminals 122 provide various user interfaces to enterprise employees to interact with the processing system 120. The interfaces include, without limitation, interfaces to input and adjust bio-algorithms; review energy usage data and/or scores; to retrieve data related to user contracts; and/or to manually adjust an allocation amount. In some instances, different users may be given different access privileges. For example, marketing employees may only be able to retrieve information about users but not make any changes to data. Such interfaces may be integrated into one or more websites for managing the enterprise system 108 presented by the application servers 112, or they may be integrated into thin or thick software clients or stand-alone software. The company terminals 122 can be any computing devices suitable for carrying out the processes described above, including personal computers, laptop computers, tablet computers, smartphones, servers, and other computing devices.

The user terminal 130 provides various user interfaces to users to interact with the enterprise system 108 over the communications network 150. Potential users can use user terminals 130 to input user information, select bio-algorithms, and/or retrieve contract and pricing information for subsidies offered by the enterprise. Users can enter information pertaining to energy usage and/or changes in their contract, e.g., an addition or subtraction of user lighting fixtures 104, etc.

In some embodiments, the user communication hub 102 may not be continually connected to the enterprise system 108 via the network 150. For example, the user communication hub 102 may be configured to temporarily store data if the user communication hub 102 becomes disconnected from the network 150. When the connection is restored, the user communication hub 102 can then transmit the temporarily stored data to the enterprise system 108. The user communication hub 102 may alternatively be configured to connect to the communications network 150 through a user's home Wi-Fi network. In this case, the user communication hub 102 stores energy usage data until a predetermined time, connects to the user's wireless network, and sends the data. In some embodiments, the user communications hub 102 is not connected to the network 150 at all, but rather, data collected is transmitted to the enterprise through other means. For example, a user can receive a user communication hub 102 from the enterprise, couple the device 104 to his or her light fixtures 104, and then either mail the device 104 with the collected data to the enterprise system 108 or extract and send the collected data to the enterprise system 108 via mail, email, or through a website.

Thus, in some embodiments, the communication hub 102 may facilitate the collection and exchange of information associated with the system 100. In other embodiments, the light fixtures 104 themselves may form a computer "mesh network." As used herein, the phrase "mesh network" may refer to a network topology having a decentralized design in which each node on the network may connects to multiple other nodes. Moreover, some of the network nodes may "talk" directly to each other without requiring the assistance of an Internet connection (helping reduce the chance of a single point of failure). If one node can no longer operate, the remaining nodes may still communicate with each other, directly or through one or more intermediate nodes. Note that a mesh networks might use a full mesh topology or a partial mesh topology. Also note that one or more of the nodes may be selected as a "master node" (which can be replaced, such as when the master node fails for any reason). Further note that any of the embodiments described herein might be implemented utilizing cloud computing. For example the hub might upload data to the cloud and receive instructions back from an application executing within the cloud (and use those instructions, for example, to facilitate control of the lighting fixtures 104).

Although the element described with respect to FIG. 1 is a light fixture 104, note that similar systems may be associated with other residential appliances that may be located at and/or service the residence (e.g., water, heating, and/or cooling fixtures). Further, in addition to, or instead of, the light fixtures, a set of sensors might collect and/or transmit information about the home environment. For example, the sensor might detect a level of light, motion, temperature, a presence of volatile organic compounds, air quality, and data from another sensor. In some embodiments, a set of sensors (including light fixtures 104 and/or other types of sensors) might create an ecosystem that may be monitored and used to made adjustments to the home environment. For example, a wearable device (e.g., that measures a person's heartbeat), a bed mattress pad (e.g., that measures the quality of a person's sleep), a thermostat, might form a circuit of monitoring devices can feed data through a network that may be used to control and/or adjust lighting characteristics and/or other features of the home environment (e.g., by reducing the temperature in a bedroom by a personalized amount when a particular person goes to bed). Moreover, some embodiments might be associated with one or more devices outside the home environment, such as device in a vehicle, including an automobile, a boat, a snowmobile, and/or an airplane.

Figure 2:
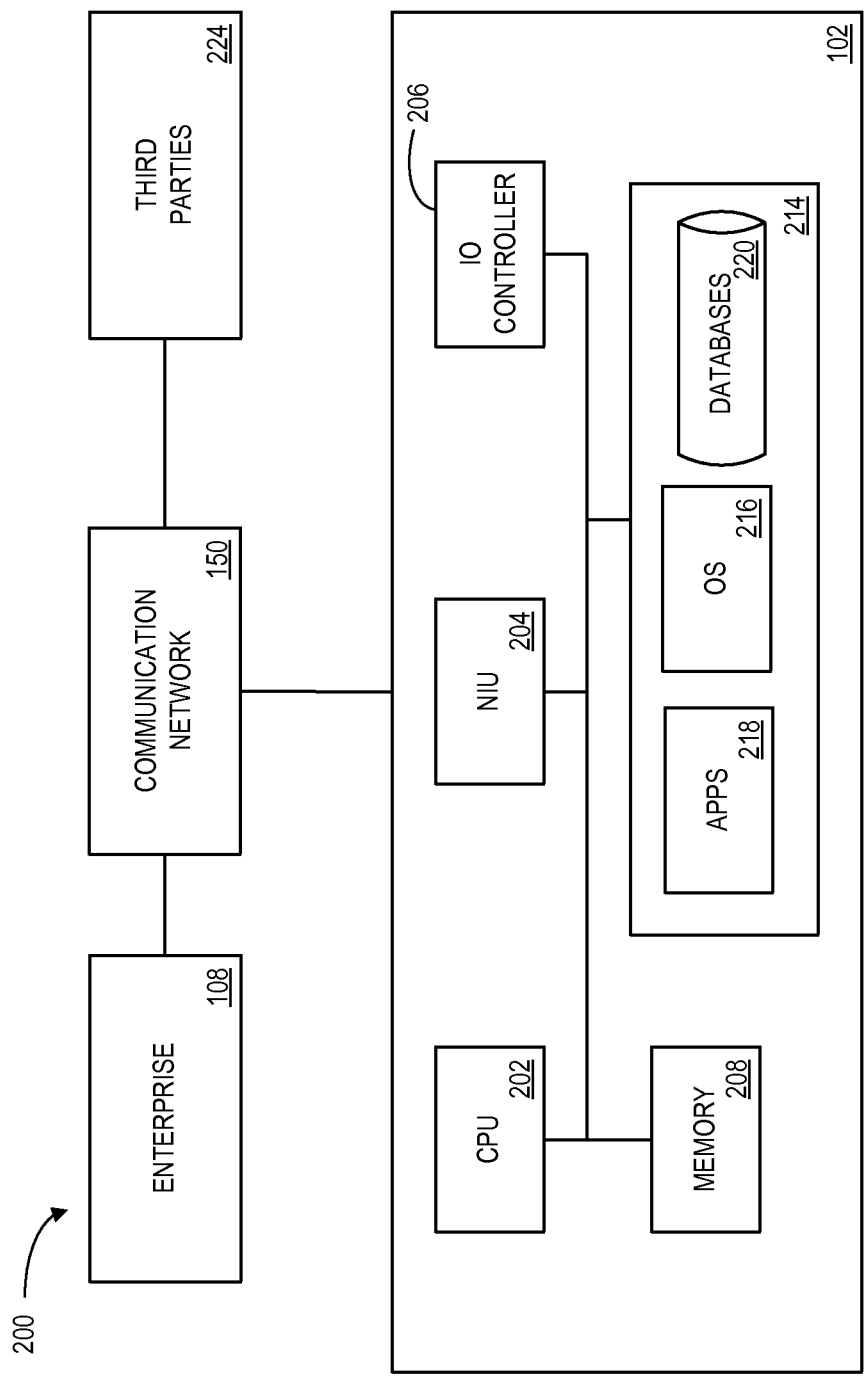
FIG. 2 is a block diagram of a computing system that may be associated with FIG. 1 according to an illustrative embodiment of the invention.

FIG. 2 is a block diagram of a computing device 200 that may be associated with the system 100 of FIG. 1 according to an illustrative embodiment of the invention. The computing device 200 comprises at least one Network Interface Unit ("NIU") 204, an Input Output ("IO") controller 206, a memory 208, and one or more data storage devices 214. The memory 208 may include at least one Random Access Memory ("RAM") and at least one Read-Only Memory ("ROM"). All of these elements are in communication with a Central Processing system ("CPU") 202 to facilitate the operation of the computing device 200. The computing device 200 may be configured in many different ways. For example, the computing device 200 may be a conventional standalone computer or alternatively, the functions of computing device 200 may be distributed across multiple computer systems and architectures. The computing device 200 may be configured to perform some or all of the bio-algorithm processing, or these functions may be distributed across multiple computer systems and architectures. In the embodiment shown in FIG. 2, the computing device 200 is linked, via network 150 or a local network, to other servers or systems housed by the enterprise system 108, such as the load balancing server and/or the application servers of FIG. 1.

The computing device 200 may be configured in a distributed architecture, wherein databases and processors are housed in separate units or locations. The computing device 200 may also be implemented as a server located either on site near the enterprise system 108, or it may be accessed remotely by the enterprise system 108. Some such units perform primary processing functions and contain at a minimum a general controller or the CPU 202 and the memory 208. In such an embodiment, each of these units is attached via the NIU 204 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP. Note that embodiments described herein may communicate via any type of communication network, including, for example, a Personal Area Network ("PAN"), a Wireless PAN ("WPAN"), a Local Area Network ("LAN"), a Wide Area Network ("WAN"), a Near Field Communication ("NFC") network, a Body Area Network ("BAN"), and/or the Internet. Moreover, as used herein the term BLUETOOTH™ may refer to, for example, BLUETOOTH™ Low Energy ("BLE") and/or BLUETOOTH™ Smart, low energy, and/or battery powered technologies.

The CPU 202 might comprise a processor, such as one or more conventional microprocessors and one or more supplementary co-processors such as math co-processors for offloading workload from the CPU 202. The CPU 202 is in communication with the NIU 204 and the IO controller 206, through which the CPU 202 communicates with other devices such as other servers, user terminals, or devices. The network NIU 204 and/or the IO controller 206 may include multiple communication channels for simultaneous communication with, for example, other processors, servers or client terminals. Devices in communication with each other need not be continually transmitting to each other. On the contrary, such devices need only transmit to each other as necessary, may actually refrain from exchanging data most of the time, and may require several steps to be performed to establish a communication link between the devices.

The CPU 202 is also in communication with the data storage device 214. The data storage device 214 may comprise an appropriate combination of magnetic, optical and/or semiconductor memory, and may include, for example, RAM, ROM, flash drive, an optical disc such as a compact disc and/or a hard disk or drive. The CPU 202 and the data storage device 214 each may be, for example, located entirely within a single computer or other computing device; or connected to each other by a communication medium, such as a USB port, serial port cable, a coaxial cable, an Ethernet type cable, a telephone line, a radio frequency transceiver or other similar wireless or wired medium or combination of the foregoing. For example, the CPU 202 may be connected to the data storage device 214 via the network interface unit 204.

The CPU 202 may be configured to perform one or more particular processing functions. For example, the computing device 200 may be configured to perform bio-algorithm processing for multiple light fixtures. The same computing device 200 or another similar computing device may be configured multiple networks associated with one or more houses and users. The same computing device 200 or another similar computing device may be configured for calculating an energy bill discount for a residence or user based on these factors.

The data storage device 214 may store, for example, (i) an operating system 216 for the computing device 200; (ii) one or more applications 218 (e.g., computer program code and/or a computer program product) adapted to direct the CPU 202 in accordance with the present invention, and particularly in accordance with the processes described in detail with regard to the CPU 202; and/or (iii) database(s) 220 adapted to store information that may be utilized to store information required by the program. The database(s) 220 may including all or a subset of data stored in enterprise database 116, described above with respect to FIG. 1, as well as additional data, such as formulas or manual adjustments, used in establishing allocations.

The operating system 216 and/or applications 218 may be stored, for example, in a compressed, an uncompiled and/or an encrypted format, and may include computer program code. The instructions of the program may be read into a main memory of the processor from a computer-readable medium other than the data storage device 214, such as from the ROM 212 or from the RAM 210. While execution of sequences of instructions in the program causes the CPU 202 to perform the process steps described herein, hard-wired circuitry may be used in place of, or in combination with, software instructions for implementation of the processes of the present invention. Thus, embodiments of the present invention are not limited to any specific combination of hardware and software.

Suitable computer program code may be provided for using a bio-algorithm to control a light fixture or user over a period of time. The program also may include program elements such as an operating system, a database management system and "device drivers" that allow the processor to interface with computer peripheral devices (e.g., a video display, a keyboard, a computer mouse, etc.) via the IO controller 206.

The term "computer-readable medium" as used herein refers to any non-transitory medium that provides or participates in providing instructions to the processor of the computing device (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include Dynamic Random Access Memory ("DRAM"), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or Electronically Erasable Programmable Read-Only Memory ("EEPROM"), a FLASH-EEPROM, any other memory chip or cartridge, or any other non-transitory medium from which a computer can read.

Various forms of computer readable media may be involved in carrying one or more sequences of one or more instructions to the CPU 202 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

Figure 3:
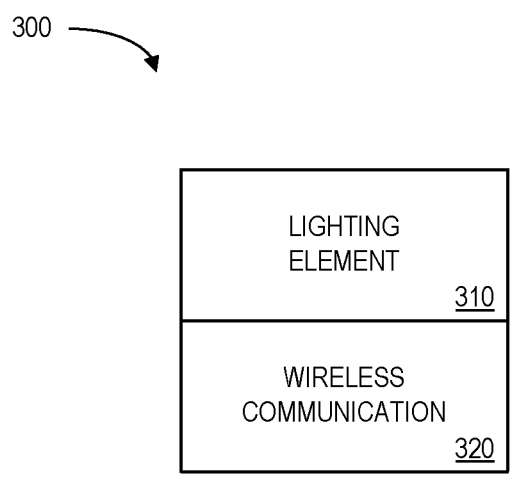
FIG. 3 is a block diagram of a light element and a device coupled to the lighting for providing data, according to an illustrative embodiment of the invention.

FIG. 3 is a block diagram of a light fixture 300 having a lighting element 310 and a wireless communication portion 320. The lighting element 310 might be associated with an LED unit or any other type energy efficient source of illumination. The wireless communication portion 320 may be co-located and/or located within the lighting element 410. According to some embodiments, the wireless communication portion 320 receives data via a household electrical system and/or to the user communication hub 102 though a wireless connection, e.g., BLUETOOTH or Wi-Fi (e.g., and the received data may be used to control a lighting characteristic of the lighting element 310). Data obtained by the user communication hub 102 from the light fixture 300 may also be reported to the enterprise. In some embodiments, the wireless portion 320 turns on automatically when the light fixture 300 is turned on; moreover, the wireless communication portion 320 may be powered by the light fixture 300.

Figure 4:
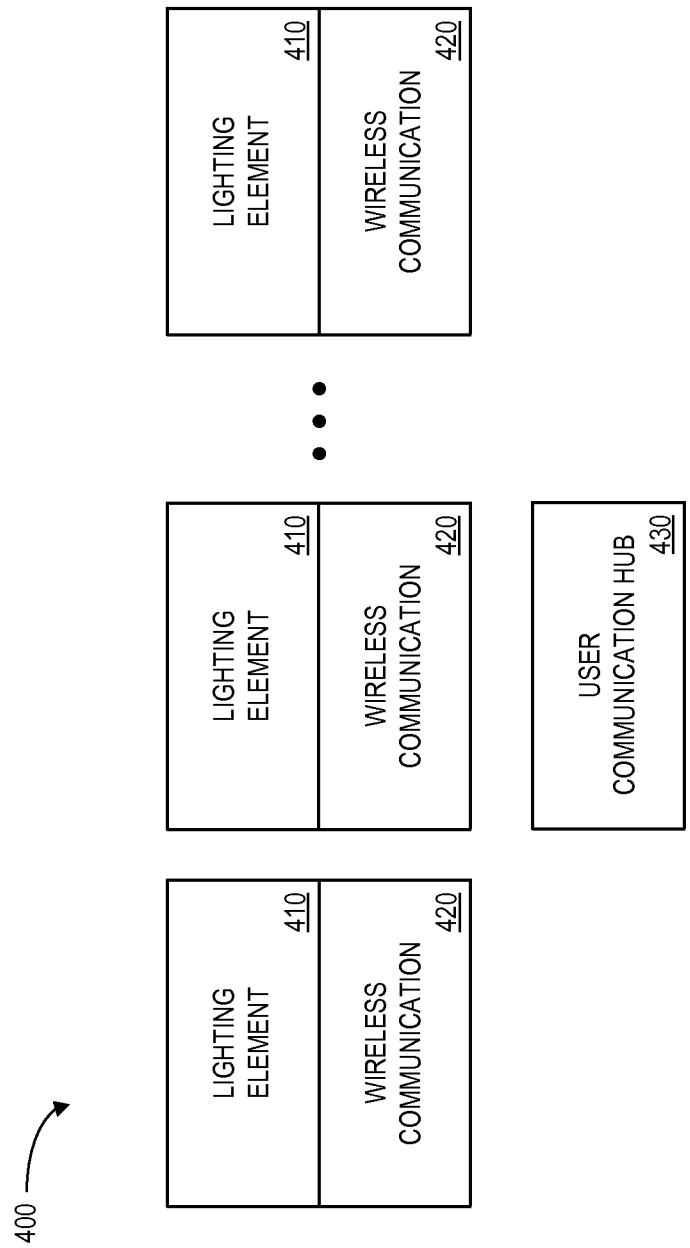
FIG. 4 illustrates a light fixture network in accordance with some embodiment of the invention.

FIG. 4 is a block diagram of a network 400 having a number of light fixtures (each with a lighting element 410 and a wireless communication portion 420). The light elements 410 might be associated with an LED unit or any other type energy efficient source of illumination. The wireless communication portions 420 may be co-located and/or located within the lighting elements 410. According to some embodiments, all of the wireless communication portions 420 transmit data to a user communication hub 430 though a wireless connection, e.g., BLUETOOTH or Wi-Fi. The communication hub 430 may use a bio-algorithm to calculate a lighting parameter to be transmitted to the wireless communication portions 420 as appropriate. Data obtained by the user communication hub 430 from the light fixtures may also be reported to the enterprise. The user communication hub 430 may also include a wireless communications device for sending collected data, including data indicative of energy consumption and scoring and receiving commands from the data processing service 106 and/or enterprise system 108 via the network 150 of FIG. 1. The user communication hub 430 may also be configured for communication with the user or a resident via a user interface. The user interface might include output components, such as a screen or speakers, and input components, such as a touch screen, keyboard, or microphone. The user interface can facilitate entry of user information, selection of bio-algorithms, etc.

Figure 5:
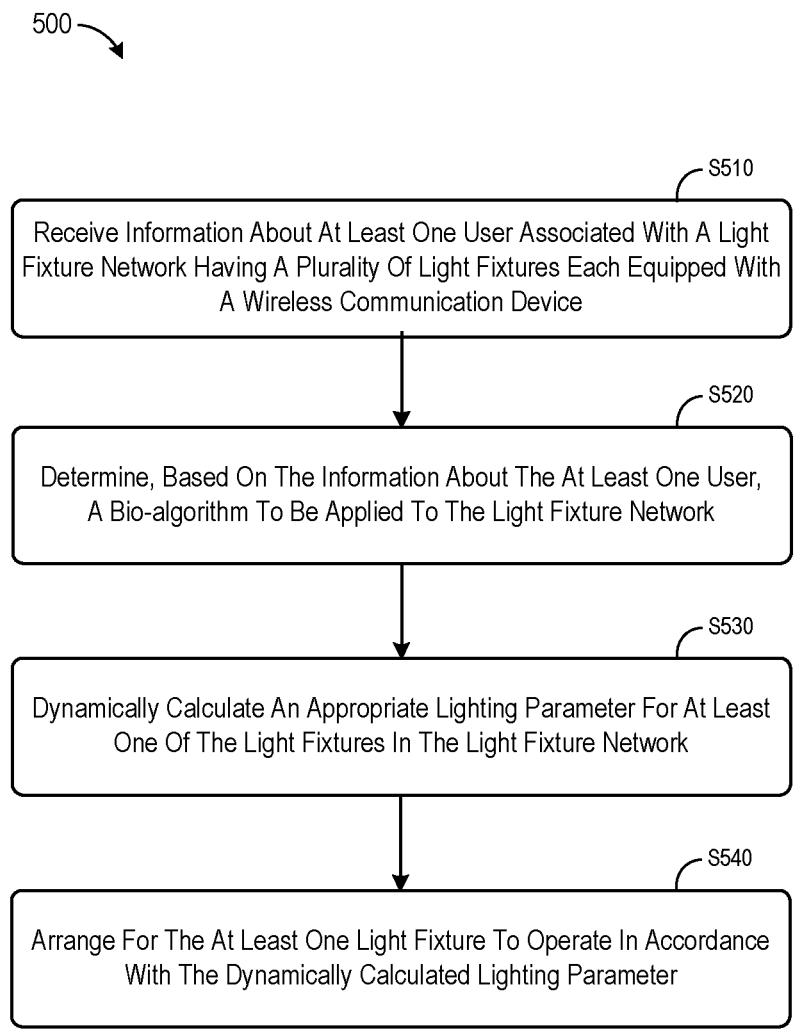
FIG. 5 is a flowchart of a method according to an illustrative embodiment of the invention.

FIG. 5 is a flowchart of a method 500 in accordance with some embodiments. The method 500 might be performed by the user communication hub 102, the data processing service 106, the enterprise system 108, or any combination of these. At S510, information may be received about at least one user associated with a light fixture network having a plurality of light fixtures (e.g., energy efficient LED light fixtures) each equipped with a wireless communication device. The information about the at least one user may be received, for example, from the user via a graphical user interface. Note that the user information might include a user age, a user gender, a user work schedule, user sleep habits, user medical information, a user identifier, a wearable user activity tracker, and/or a mattress sensor.

At S520, it may be determined, based on the information about the at least one user, a bio-algorithm to be applied to the light fixture network. According to some embodiments, the user simply selects the bio-algorithm from a list of potential bio-algorithms, such as a healthy lifestyle program, a mental acuity program, a sleep cycle optimization program, insomnia treatment, a dementia reduction program, a circadian cycle, a Seasonal Affective Disorder ("SAD") treatment, depression, and/or Sundown Syndrome.

At S530, a dynamic calculation may generate an appropriate lighting parameter for at least one of the light fixtures in the light fixture network. The dynamic calculation might be associated with, for example, energy efficiency, air quality, temperature, calories, a motion sensor, a user location within a residence, multiple users, a window shade (e.g., indicating whether or not the shade is pulled down), a heating or cooling system, an entertainment system, a pet monitoring system, a child monitoring system, a pool monitoring system, a water monitoring system, a time of day, a day of week, a day of year, a season, a holiday, a safety and security system (e.g., associated with alarm or health monitoring devices), a wearable device, and/or a bed mattress pad.

At S540, it may be arranged for the at least one light fixture to operate in accordance with the dynamically calculated lighting parameter. The lighting parameter might be associated with, for example, a luminescence, a wattage, a color characteristic, a correlated color temperature, and/or a wavelength. According to some embodiments, at least some of the light fixtures are further equipped with a sensor, and a processor may be further configured to collect sensor information from the light fixture network.

Figure 6:
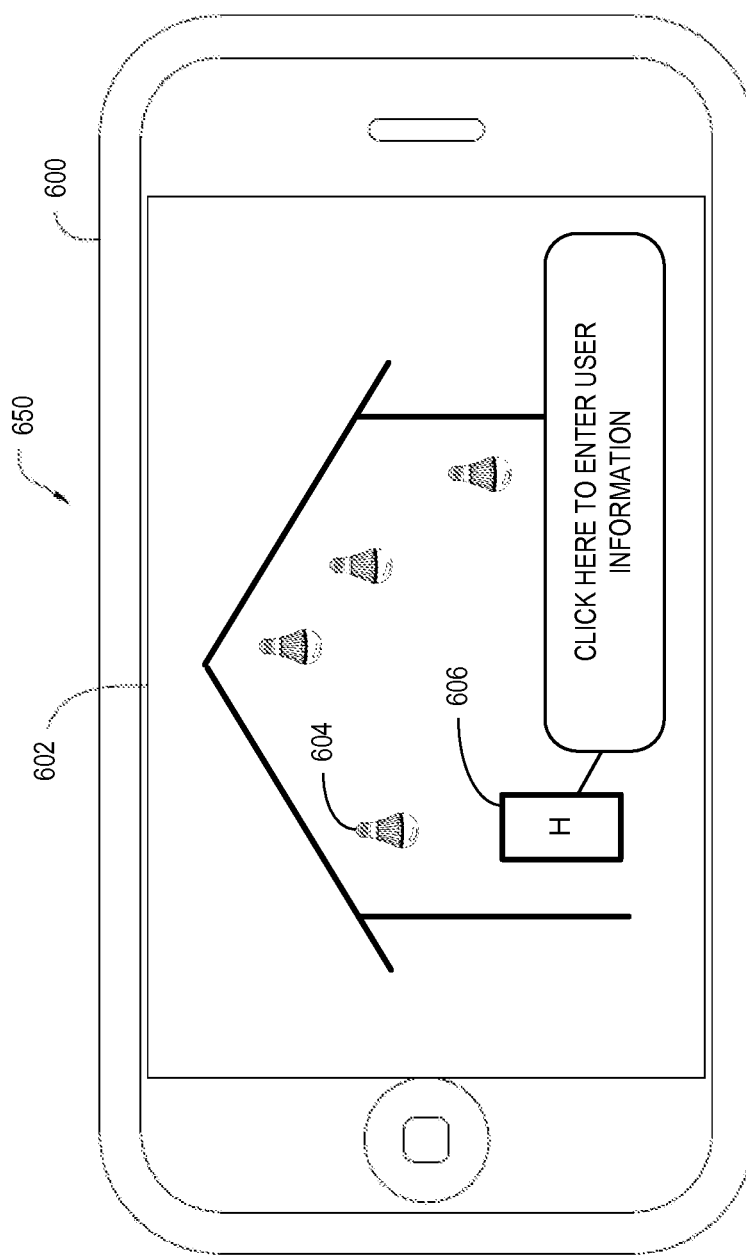
FIGS. 6 and 7 illustrate network displays in accordance with some embodiments described herein.
Figure 7:
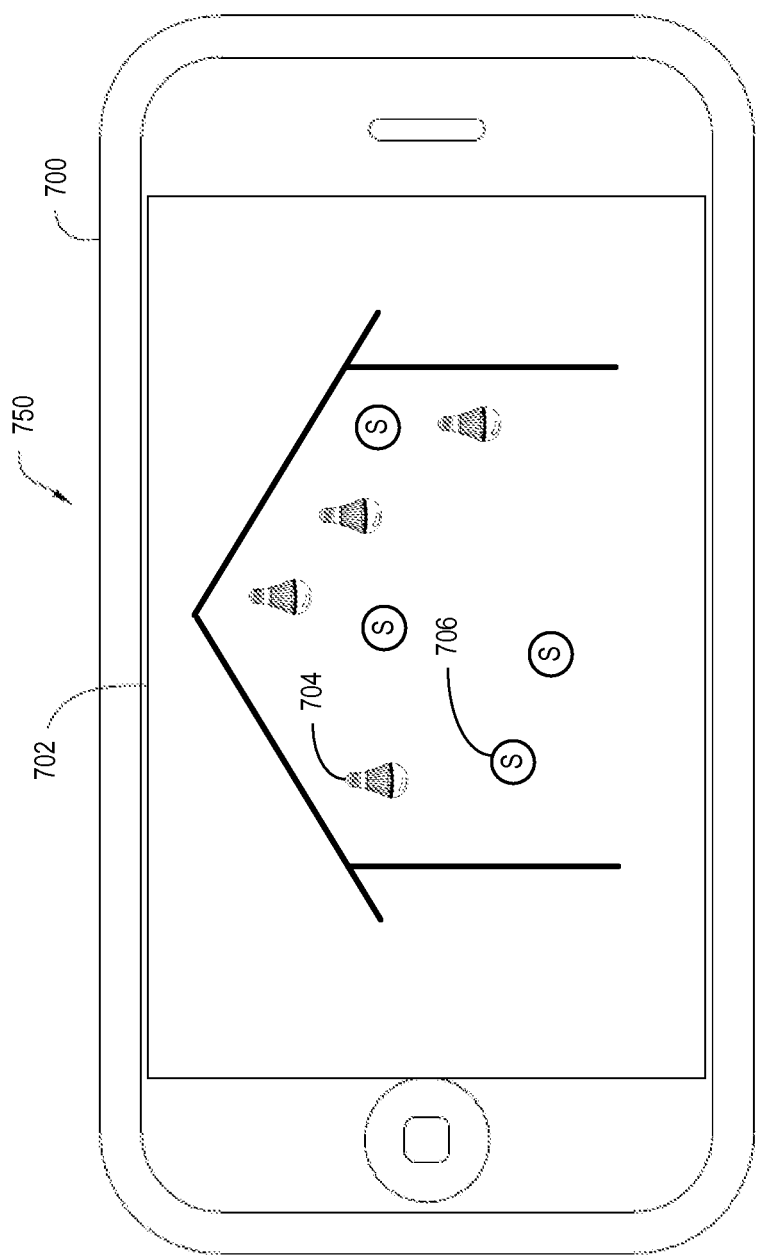

According to some embodiments, information about a home light fixture network may be displayed to a user on a display. For example, referring now to FIG. 6, a diagram 650 depicting a user interface 602 is shown. The user interface 602 may be displayed on device 600 such as a mobile telephone, PDA, personal computer, or the like. For example, the device 600 may be a PC, an iPhone® or smartwatch from Apple, Inc., a BlackBerry® from RIM, a mobile phone using the Google Android® operating system, or the like. The user interface 602 depicts a portion of a user's home. The user interface 602 may display locations of light fixtures 604 and/or a communication hub "H" 606. In this way, a user may be able to quickly view the status of his or her network. According to some embodiments, selecting the H icon 606 results in a user being able to enter information about his or her preferences, select a bio-algorithm, etc. As another example, referring now to FIG. 7, a diagram 750 depicting a user interface 702 is shown. The user interface 702 again depicts the user's house including light fixtures 704. In this embodiment, information about one or more sensors 706 also displayed. The user interface 702 may display sensor associated with other systems in the user's home, such as an air conditioning system and/or heating system.

Figure 8:
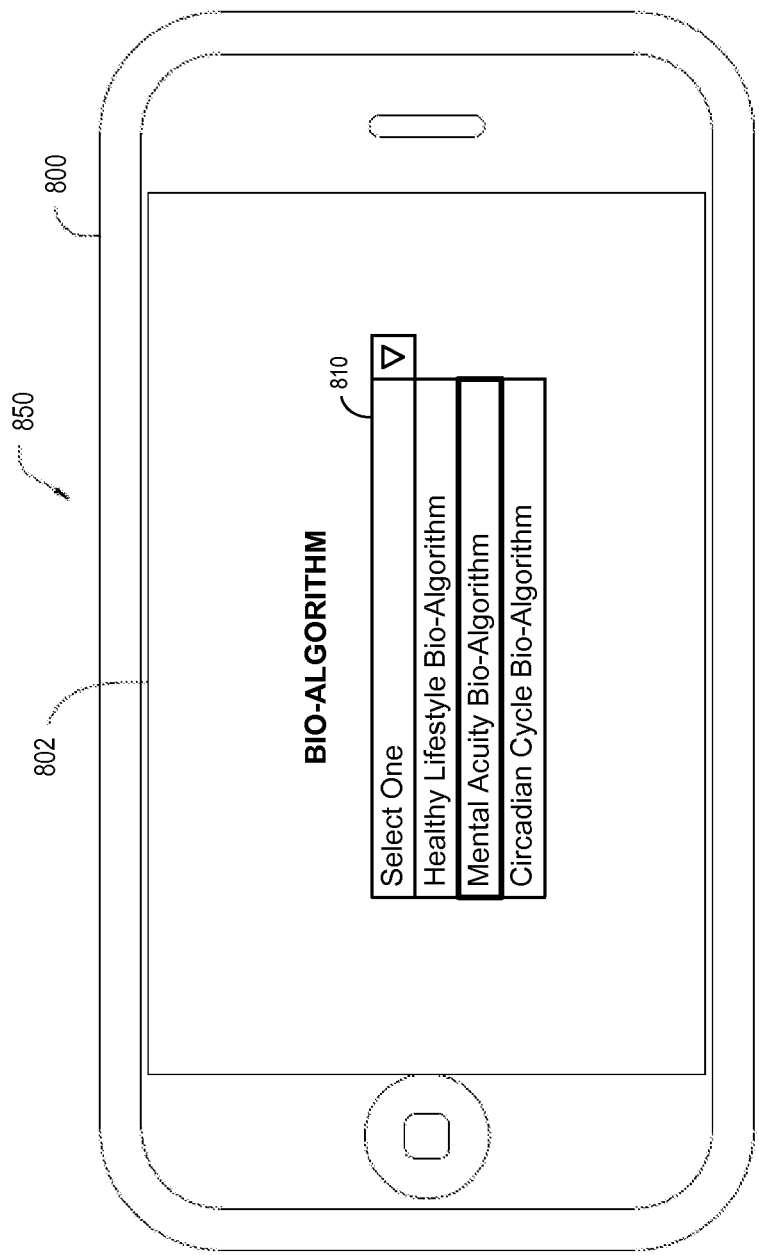
FIGS. 8 through 12 illustrate user information displays according to some embodiments.

The light fixtures 704 may be controlled based on a bio-algorithm that was previously selected by a user. For example, FIG. 8 is a diagram 850 depicting a user interface 802 displayed on a device 800. The user interface 802 includes a drop-down bio-algorithm selection area 810 that can be accessed by a user to select an appropriate bio-algorithm (e.g., to promote a healthy lifestyle, mental acuity, etc.).

Figure 9:
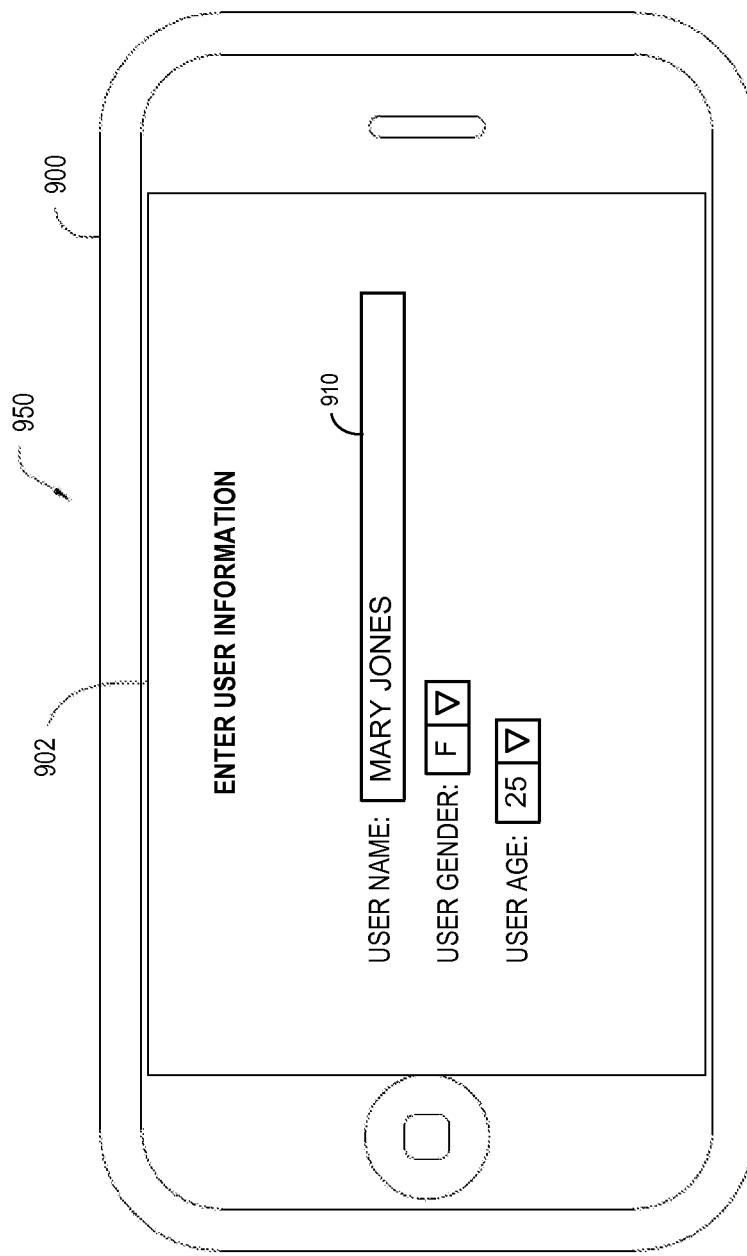

Other information about a user may also be used to control light fixtures. For example, FIG. 9 is a diagram 950 depicting a user information interface 902 displayed on a device 900. The user information interface 902 includes a data entry portion 910 where a user may enter, for example, his or her name, gender, and age (or date of birth). This information may then be used to select an appropriate bio-algorithm or adjust values associated with a selected bio-algorithm. For example, very different light characteristics might be appropriate for young children, teenagers, and/or the elderly.

Figure 10:
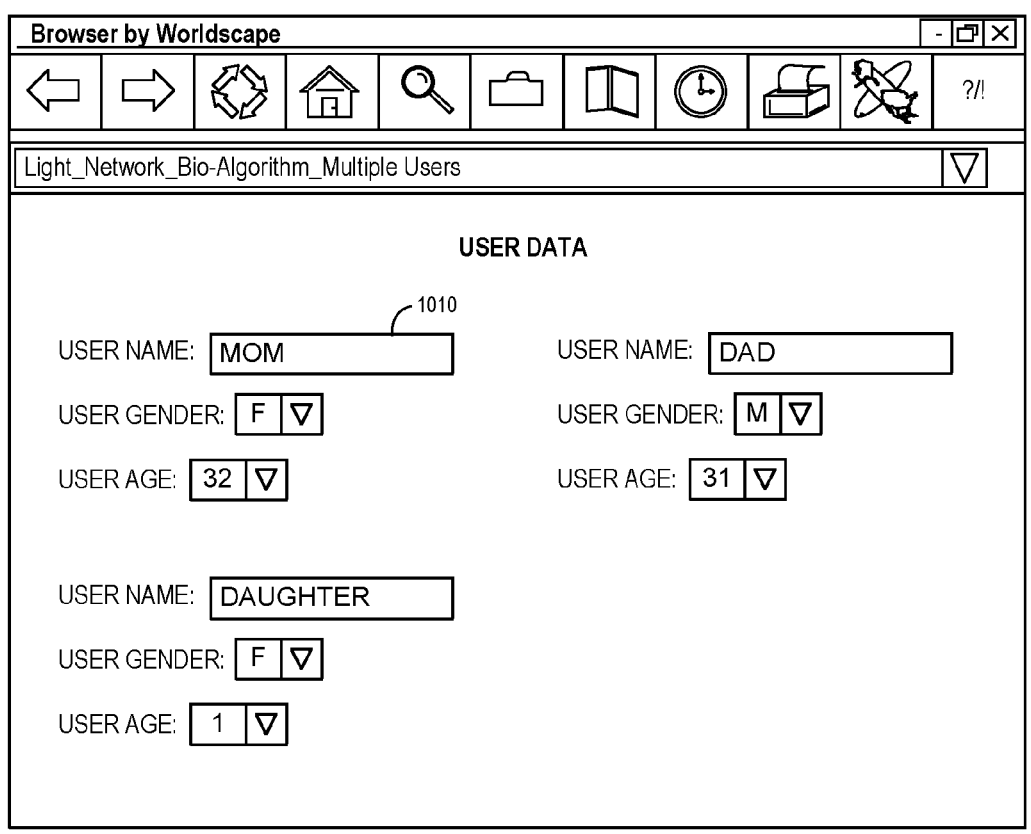

In some cases, a system may monitor and/or support multiple users within a home. For example, FIG. 10 is a web-based multi-user data display 1000 according to some embodiments. The display 1000 includes user data entry portions 1010 for a number of different users (e.g., and each may be used to enter a name, gender, and age). This information may then be used to select an appropriate bio-algorithm or adjust values associated with a selected bio-algorithm. Note the different bio-algorithms might be selected for different users, and, according to some embodiments, appropriate decisions are made to control various light fixtures as each user moves throughout a house.

Figure 11:
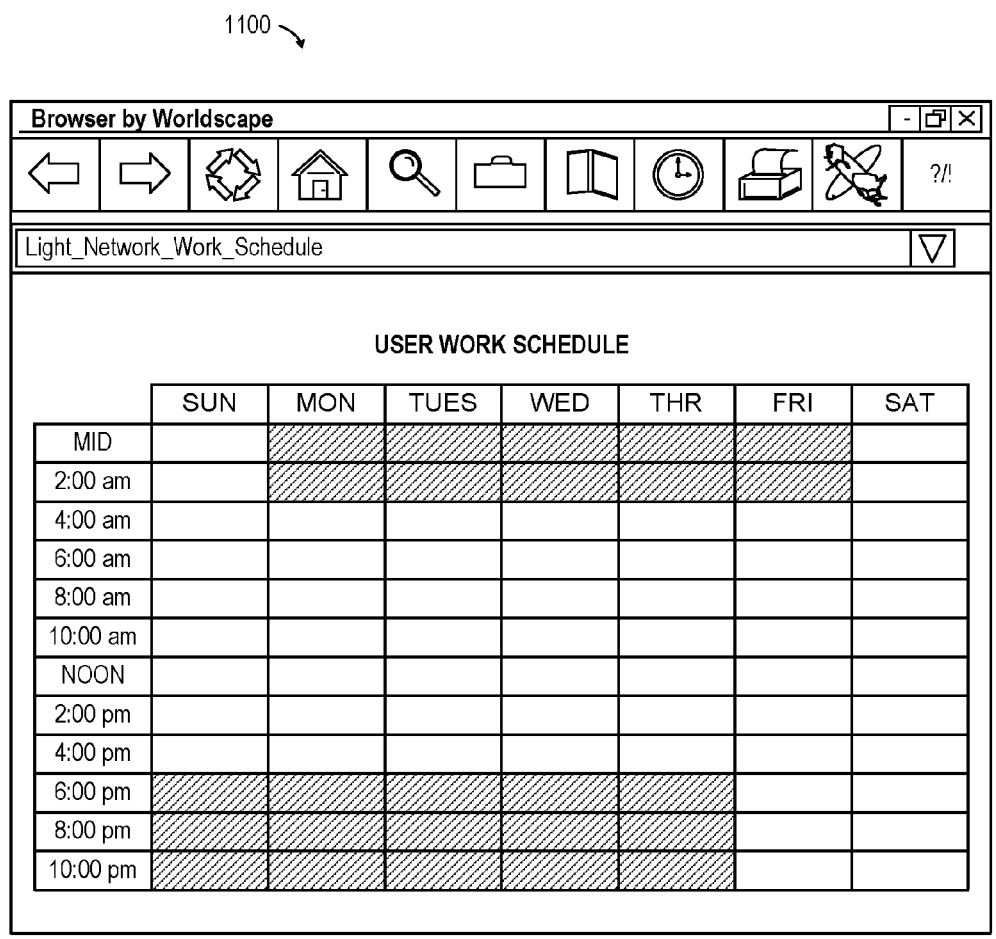

According to some embodiments, information about a user's work schedule may be used to control light fixtures. For example, FIG. 11 is a web-based work schedule display 1100 according to some embodiments. The display 1100 includes a graphical schedule that a user can access to enter his or her work schedule (e.g., as illustrated in FIG. 11, the cross-hatched area indicates that the user is working night shifts). As a result, an appropriate bio-algorithm may be selected for the user (or adjustments to values associated with a selected bio-algorithm may be made as appropriate). Note that a user working night shifts may respond positively to different types of light as compared to a user who is working day shifts. Similar displays 1100 may be used to enter a student's school schedule and/or a sleep schedule. According to some embodiments, the system may be coupled to another calendar application (e.g., on a user's smartphone) and this information may be automatically pre-populated.

Figure 12:
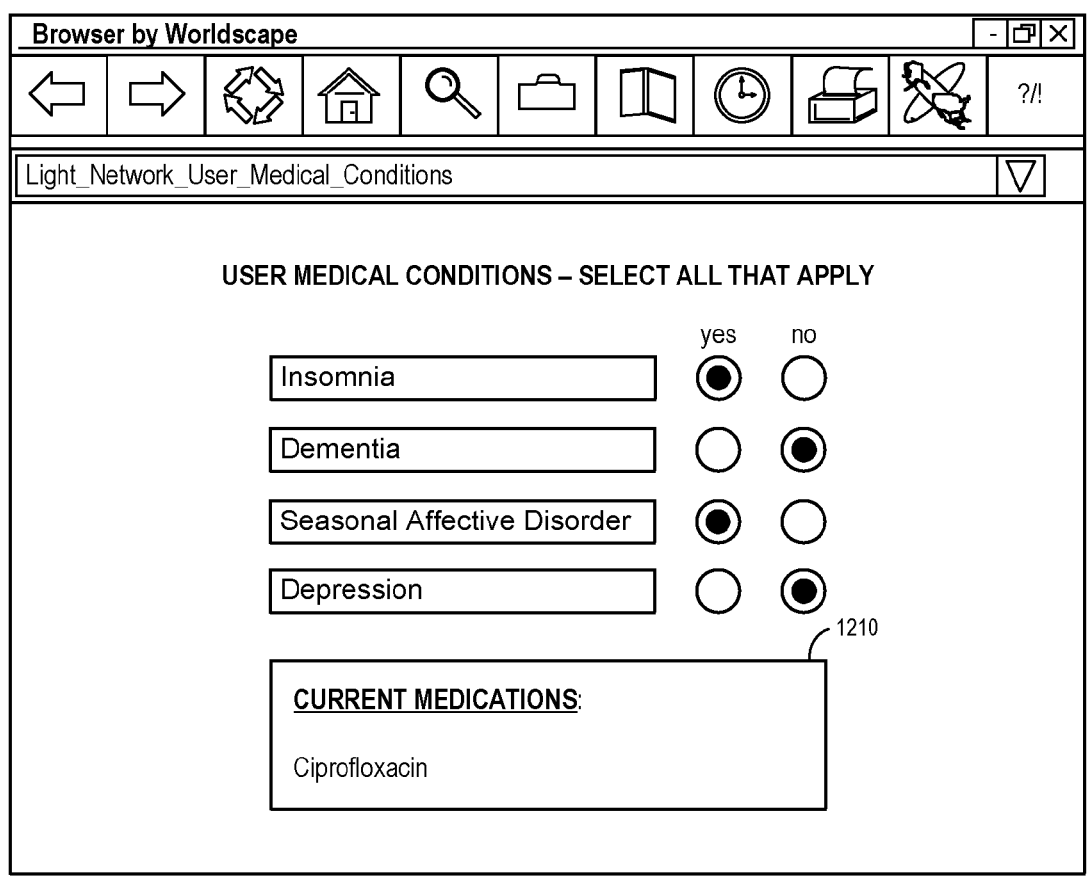

Information about a user's current medical conditions and/or history may also be used to control light fixtures. For example, FIG. 12 is web-based medical information display 1200 according to some embodiments. The medical information display 1200 includes a data entry portion where a user can indicate if he or she has various medical conditions (e.g., insomnia or depression). Based on this information, an appropriate bio-algorithm may be selected for the user (or adjustments to values associated with a selected bio-algorithm may be made to help treat the user's condition as appropriate). According to some embodiments, some or all of this information might be received from a user's wearable activity tracker (e.g., his or her current heartbeat), an electronic medical record, etc. Note that the medical condition information described herein is provided only as an example, and any other types of medical condition information might be used in connections with the embodiments described herein. For example, a user's sleep scorecard might be manually or automatically updated, a dietary history might be utilized, and/or a list of medications and/or supplements taken by a customer might be manually or automatically tracked. In some embodiments, one or more light characteristics might be selected based on photosensitivity and/or phototoxic drug interactions associated with medications currently being taken 1210 by a user (including, for example, those associated with antibiotics, such as doxycycline, ciprofloxacin, and/or trimethoprim). For example, particular light bulbs could be "tuned" so as to increase and/or avoid certain sunlight Kelvin scale frequencies to avoid negative reactions and/or even improve a medication's effect for the user.

Figure 13:
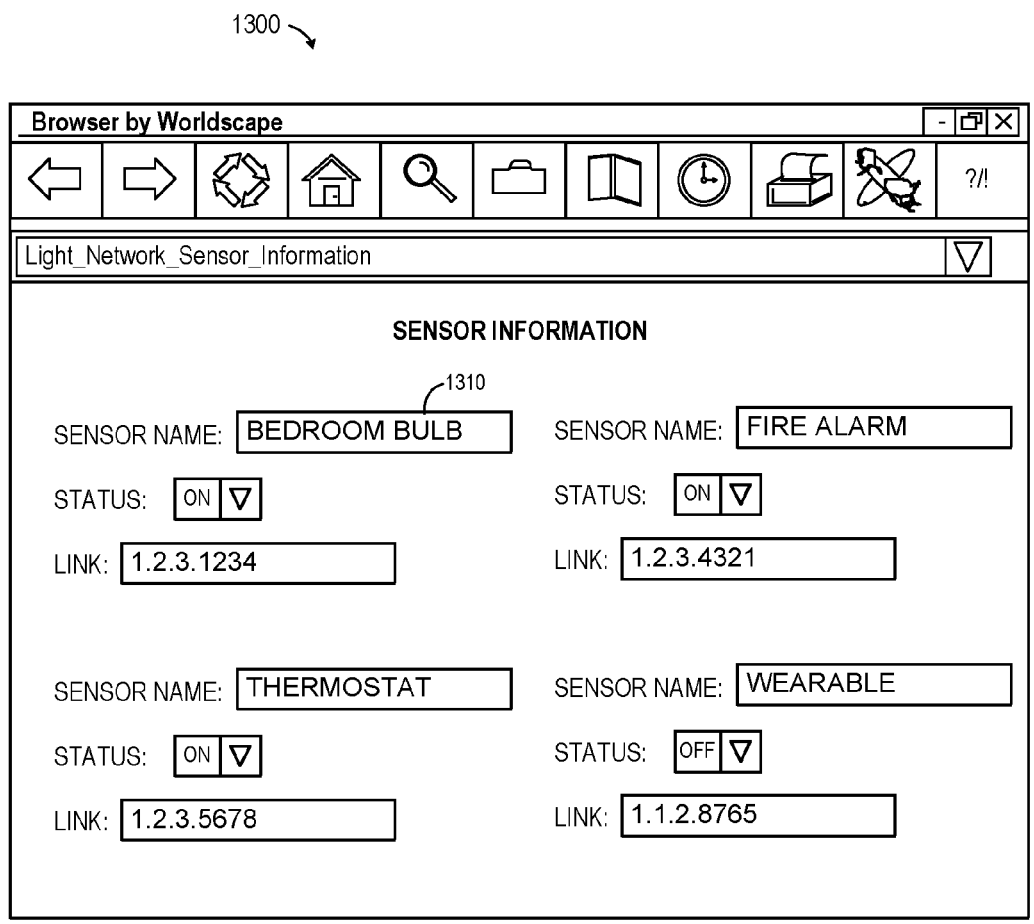
FIG. 13 illustrates a sensor information display according to some embodiments.

Sensor information may be used to select an appropriate bio-algorithm or to determine if a currently selecting bio-algorithm is working as intended. For example, FIG. 13 illustrates a sensor information display 1300 according to some embodiments. The sensor information display 1300 includes a data entry area where a user can provide a sensor name, a sensor status (e.g., on, off, dim, standby, etc.), and link information (e.g., an IP address that can be used to receive information from and/or send information to the sensor. Examples of sensors include energy efficient light fixtures, thermostats, a fire alarm or other air quality sensor, movement detectors, wearable devices (e.g., a smartwatch), etc.

Figure 14:
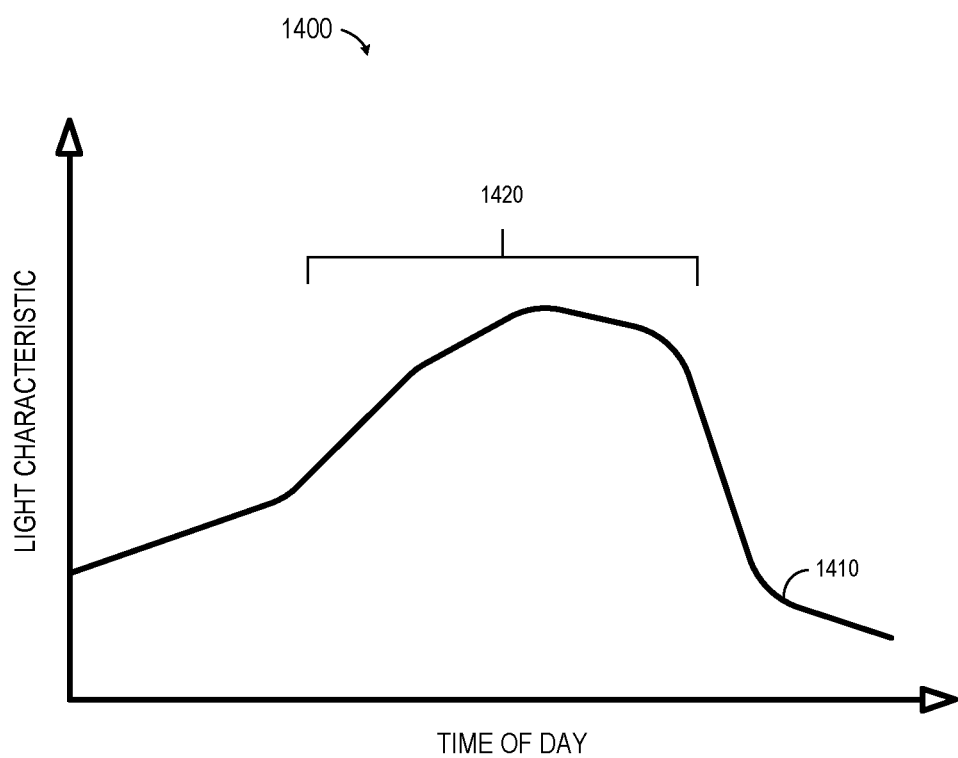
FIG. 14 illustrates how a light characteristic might change during a day according to some embodiments.

According to some embodiments, a bio-algorithm automatically and dynamically calculates an appropriate lighting parameter that can be transmitted to a light fixture to control at least one characteristic of the light emitted from that fixture. FIG. 14 illustrates how a light characteristic might change during a day 1400 according to some embodiments. In particular, a light characteristic 1410 is elevated during a particular portion 1420 of the day. As used herein, the phrase "light characteristic" might refer to, for example, a color temperature that expresses the color appearance of the light itself The color temperature refers to the way color groups are perceived and is associated with a psychological and/or physiological impact of lighting. The color temperature may refer to how cool or warm the light appears and a temperature may be expressed as a numerical measurement as measured in degrees Kelvin (K). Colors from the red/orange/yellow side of the spectrum are described as warm (incandescent) while those toward the blue end are referred to as cool, such as natural daylight. The sun, for example, rises at approximately 1800K and increases to 5000K at noon. Other examples of a light parameter that might be automatically calculated in connection with a bio-algorithm include lumens, watts, and/or Color Rendering Index ("CRI") values.

Figure 15:
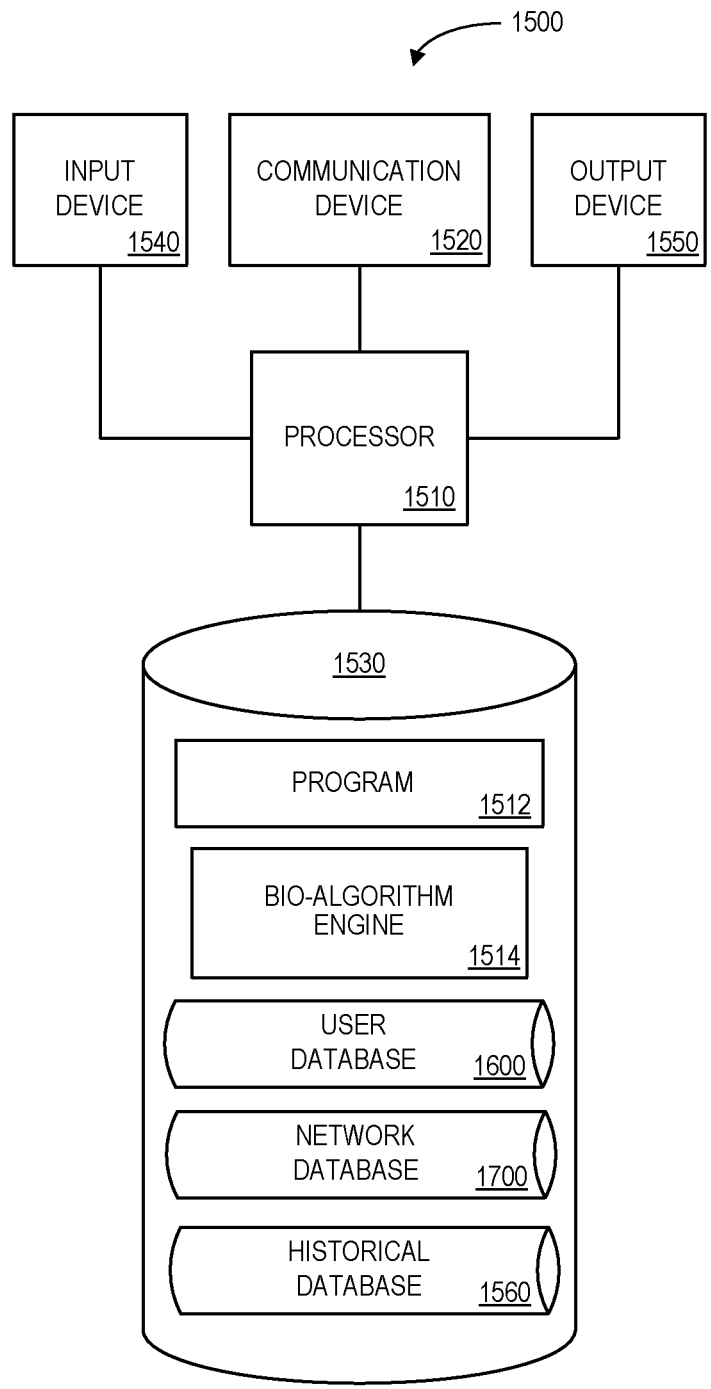
FIG. 15 is a block diagram of a bio-algorithm platform provided in accordance with some embodiments.

The processes described herein may be performed by any suitable device or apparatus. FIG. 15 is one example of a bio-algorithm platform 1500 according to some embodiments. The bio-algorithm platform 1500 may be, for example, associated with the system 108 of FIG. 1. The bio-algorithm platform 1500 comprises a processor 1510, such as one or more commercially available CPUs in the form of one-chip microprocessors, coupled to a communication device 1520 configured to communicate via a communication network (not shown in FIG. 15). The communication device 1520 may be used to communicate, for example, with one or more remote light fixtures, user communication hubs, enterprises, and/or third party services. The bio-algorithm platform 1500 further includes an input device 1540 (e.g., a mouse and/or keyboard to enter information about bio-algorithms) and an output device 1550 (e.g., a computer monitor to display reports and/or results to an administrator).

The processor 1510 also communicates with a storage device 1530. The storage device 1530 may comprise any appropriate information storage device, including combinations of magnetic storage devices (e.g., a hard disk drive), optical storage devices, and/or semiconductor memory devices. The storage device 1530 stores a program 1512 and/or bio-algorithm engine 1514 for controlling the processor 1510. The processor 1510 performs instructions of the programs 1512, 1514, and thereby operates in accordance with any of the embodiments described herein. For example, the processor 1510 may receive information about at least one user associated with a light fixture network, having a plurality of light fixtures each equipped with a wireless communication device. A bio-algorithm to be applied to the light fixture network may then be determined by processor 1510 based on the information about the at least one user. An appropriate lighting parameter (e.g., a luminescence, a wattage, a color characteristic, and/or a wavelength) for at least one of the light fixtures in the light fixture network may be dynamically calculated by the processor 1510, and it may be arranged by processor 1510 for the at least one light fixture to operate in accordance with the dynamically calculated lighting parameter (e.g., the parameter might be transmitted to the light fixture).

Referring again to FIG. 15, the programs 1512, 1514 may be stored in a compressed, uncompiled and/or encrypted format. The programs 1512, 1514 may furthermore include other program elements, such as an operating system, a database management system, and/or device users used by the processor 1510 to interface with peripheral devices.

As used herein, information may be "received" by or "transmitted" to, for example: (i) the bio-algorithm platform 1500 from another device; or (ii) a software application or module within the bio-algorithm platform 1500 from another software application, module, or any other source.

In some embodiments (such as shown in FIG. 15), the storage device 1530 stores a user database 1600, a network database, 1700, and/or a historical database 1560. An example of databases that may be used in connection with the bio-algorithm platform 1500 will now be described in detail with respect to FIGS. 16 and 17. Note that the databases described herein are only examples, and additional and/or different information may be stored therein. Moreover, various databases might be split or combined in accordance with any of the embodiments described herein.

Figure 16:
FIG. 16 is a tabular portion of a user database in accordance with some embodiments.

Referring to FIG. 16, a table is shown that represents the user database 1600 that may be stored at the bio-algorithm platform 1500 according to some embodiments. The table may include, for example, entries identifying users. The table may also define fields 1602, 1604, 1606, 1608, 1610, 1612 for each of the entries. The fields 1602, 1604, 1606, 1608, 1610 may, according to some embodiments, specify: a user identifier 1602, an age 1604, a selected bio-algorithm 1606, medical conditions 1608, a current location 1610, and current medications. The information in the user database 1600 may be created and updated, for example, based on information received from users.

The user identifier 1602 may be, for example, a unique alphanumeric code identifying a user or potential user (e.g., a person) and the age 1604 might reflect his or her age. The selected bio-algorithm 1606 might have been automatically selected for the user or manually selected by the user. The medical conditions 1608 might indicate one or more problems being experienced by that user and the current location 1610 might indicate where he or she is (e.g., what room in the home or even that he or she is not present in the house). The age 1604, selected bio-algorithm 1606, medical conditions 1608, current location 1610, and/or current medications 1612 of each user might then be used to calculate light parameters as appropriate throughout the home.

Figure 17:
FIG. 17 is a tabular portion of a network database in accordance with some embodiments.

Referring to FIG. 17, a table is shown that represents the network database 1700 that may be stored at the bio-algorithm platform 1500 according to some embodiments. The table may include, for example, entries defining a network of light fixtures. The table may also define fields 1702, 1704, 1706, 1708, 1710 for each of the entries. The fields 1702, 1704, 1706, 1708, 1710 may, according to some embodiments, specify: a network identifier 1702, a light fixture identifier 1704, a description 1706, a temperature in Kelvin 1708, and a status 1710. The information in the enterprise database 1700 may be created and updated, for example, based on information received from a user, light fixtures, and/or user communication hubs.

The network 1702 might be, for example, a network identifier, communication address, or any other information that can associated with a light fixture with a remote user network. The light fixture identifier 1704 may be, for example, a unique alphanumeric code identifying an energy efficient light fixture. The description 1706 might, for example, indicate entity manufacturer that produced the light fixture, a room where the fixture is located, or any other information associated with the light fixture. The temperature 1708 might have been dynamically calculated for the light fixture based on the information in the user database 1600. The status 1710 might indicate, for example, whether the light fixture is currently on, off, in standby mode, dimmed, etc. As used herein, the phrase "standby mode" might indicate, for example, that a lighting element is off and the fixture is "listening" for further instructions. The information in the network database 1700 may, for example, be used to control light fixtures in a home network.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Although specific hardware and data configurations have been described herein, note that any number of other configurations may be provided in accordance with embodiments of the present invention (e.g., some of the information associated with the databases described herein may be combined or stored in external systems). Moreover, note that some or all of the embodiments described herein might collect, analyze, and/or display information about bio-algorithms in substantially real time. For example, bio-algorithms might be analyzed on a daily basis (e.g., by comparing current values to other situations at a similar time of day, with a similar number of people in a house for a similar length of time). As a result of this analysis, adjustments might be automatically applied to one or more light fixtures (e.g., to improve the user's experience). Similar adjustments might be made on an hourly, weekly, or any other periodic basis. According to some embodiments, bio-algorithms may be user-selected and/or automatically determined using a business rules engine. Note that the system might automatically prioritize selections when multiple users are present in near field occupancy zone (e.g., the users are in the same room). Moreover, remote access might let a user set and/or re-set (e.g., to a previously set state) the system, including remote access associated with system support and service functionality.

The present invention has been described in terms of several embodiments solely for the purpose of illustration. Persons skilled in the art will recognize from this description that the invention is not limited to the embodiments described, but may be practiced with modifications and alterations limited only by the spirit and scope of the appended claims.

What is claimed is:

1. A system associated with light fixtures, the system comprising:
    a communication port to receive, from a graphical user interface, information about at least one user associated with a light fixture network having a plurality of light fixtures each equipped with a wireless communication device, wherein the graphical user interface includes map information display locations of light fixtures and sensors in a user's home and the information about the at least one user includes user schedule data graphically exchanged via the graphical user interface;
    a computer memory for storing data; and a processor in communication with the computer memory, wherein the processor is configured to:
- determine, based on the information about the at least one user, a bio-algorithm to be applied to the light fixture network,
- dynamically calculate an appropriate lighting parameter for at least one of the light fixtures in the light fixture network, and
- arrange for the at least one light fixture to operate in accordance with the dynamically calculated lighting parameter.

2. The system of claim 1, wherein at least some of the light fixtures are energy efficient light emitting diode light fixtures.

3. The system of claim 2, wherein the information about the at least one user includes selection by the user of the bio-algorithm from a list of potential bio-algorithms presented via the graphical user interface.

4. The system of claim 3, wherein the selected bio-algorithm is associated with at least one of: (i) a healthy lifestyle program, (ii) a mental acuity program, (iii) a sleep cycle optimization program, (iv) insomnia treatment, (v) a dementia reduction program, (vi) a circadian cycle, (vii) a seasonal affective disorder treatment, (viii) depression, and (xiv) Sundown Syndrome.

5. The system of claim 1, wherein the information about the at least one user includes at least one of: (i) a user age, (ii) a user gender, (iii) a user work schedule, (iv) user sleep habits, (v) user medical information, (vi) a user identifier, (vii) a wearable user activity tracker, and (viii) a mattress sensor.

6. The system of claim 1, wherein the dynamic calculation is further associated with at least one of: (i) energy efficiency, (ii) air quality, (iii) temperature, (iv) calories, (iv) a motion sensor, (v) a user location within a residence, (vi) multiple users, (vii) a window shade, (viii) a heating or cooling system, (ix) an entertainment system, (x) a pet monitoring system, (xi) a child monitoring system, (xii) a pool monitoring system, (xiii) a water monitoring system, (xiv) a time of day, (xv) a day of week, (xvi) a day of year, (xvii) a season, (xviii) a holiday, (xix) a safety and security system, (xx) a wearable device, and (xxi) a bed mattress pad.

7. The system of claim 1, wherein the lighting parameter is associated with at least one of: (i) a luminescence, (ii) a wattage, (iii) a color characteristic, (iv) a correlated color temperature, and (v) a wavelength.

8. The system of claim 1, wherein at least some of the light fixtures are further equipped with a sensor, and the processor is further configured to:
- collect sensor information from the light fixture network.

9. The system of claim 8, wherein the sensor is to detect: (i) a level of light, (ii) motion, (iii) temperature, (iv) a presence of volatile organic compounds, (v) air quality, and (vi) data from another sensor.

10. The system of claim 1, wherein the communication port receives data about the light fixture network via at least one of: (i) a user communication hub co-located with the light fixture network, and (ii) one of the plurality of light fixtures wherein the light fixture network comprises a mesh network topology.

11. The system of claim 1, wherein information about multiple users associated with multiple residences is transmitted to at least one of: (i) a user device, (ii) an enterprise device, (iii) an energy company device, and (iv) a payment platform.

12. A computerized method associated with light fixtures, the method comprising:
- receiving from a graphical user interface, information about at least one user associated with a light fixture network having a plurality of light fixtures each equipped with a wireless communication device, wherein the graphical user interface includes map information display locations of light fixtures and sensors in a user's home and the information about the at least one user includes user schedule data graphically exchanged via the graphical user interface;
- determining, based on the information about the at least one user, a bio-algorithm to be applied to the light fixture network;
- dynamically calculating an appropriate lighting parameter for at least one of the light fixtures in the light fixture network; and
- arranging for the at least one light fixture to operate in accordance with the dynamically calculated lighting parameter.

13. The method of claim 12, wherein at least some of the light fixtures are energy efficient light emitting diode light fixtures.

14. The method of claim 12, wherein the information about the at least one user includes selection by the user of the bio-algorithm from a list of potential bio-algorithms presented via the graphical user interface.

15. The method of claim 14, wherein the selected bio-algorithm is associated with at least one of: (i) a healthy lifestyle program, (ii) a mental acuity program, (iii) a sleep cycle optimization program, (iv) insomnia treatment, (v) a dementia reduction program, (vi) a circadian cycle, (vii) a seasonal affective disorder treatment, and (viii) Sundown Syndrome.

16. The method of claim 14, wherein the information about the at least one user includes at least one of: (i) a user age, (ii) a user gender, (iii) a user work schedule, (iv) user sleep habits, (v) user medical information, (vi) a user identifier, (vii) a wearable user activity tracker, and (viii) a mattress sensor.

17. The method of claim 12, wherein the dynamic calculation is further associated with at least one of: (i) energy efficiency, (ii) air quality, (iii) temperature, (iv) calories, (iv) a motion sensor, (v) a user location within a residence, (vi) multiple users, (vii) a window shade, (viii) a heating or cooling method, (ix) an entertainment method, (x) a pet monitoring method, (xi) a child monitoring method, (xii) a pool monitoring method, and (xiii) a water monitoring method.

18. The method of claim 12, wherein the lighting parameter is associated with at least one of: (i) a luminescence, (ii) a wattage, (iii) a color characteristic, (iv) a correlated color temperature, and (v) a wavelength.

19. A non-transitory, computer readable medium having stored therein instructions that, upon execution, cause a computer to perform a method associated with light fixtures, the method comprising:
- receiving, via a graphical user interface, information about at least one user associated with a light fixture network having a plurality of light fixtures each equipped with a wireless communication device, wherein the graphical user interface includes map information display locations of light fixtures and sensors in a user's home and the information about the at least one user includes user schedule data graphically exchanged via the graphical user interface;
- determining, based on the information about the at least one user, a bio-algorithm to be applied to the light fixture network;

dynamically calculating an appropriate lighting parameter for at least one of the light fixtures in the light fixture network; and arranging for the at least one light fixture to operate in accordance with the dynamically calculated lighting parameter.

20. The medium of claim 19, wherein at least some of the light fixtures are energy efficient light emitting diode light fixtures.

21. The medium of claim 19, wherein the information about the at least one user includes selection by the user of the bio-algorithm from a list of potential bio-algorithms presented via the graphical user interface.

22. The medium of claim 21, wherein the selected bio-algorithm is associated with at least one of: (i) a healthy lifestyle program, (ii) a mental acuity program, (iii) a sleep cycle optimization program, (iv) insomnia treatment, (v) a dementia reduction program, (vi) a circadian cycle, (vii) a seasonal affective disorder treatment, and (viii) Sundown Syndrome.

23. The medium of claim 19, wherein the information about the at least one user includes at least one of: (i) a user age, (ii) a user gender, (iii) a user work schedule, (iv) user sleep habits, (v) user medical information, (vi) a user identifier, (vii) a wearable user activity tracker, and (viii) a mattress sensor.

24. The medium of claim 19, wherein the dynamic calculation is further associated with at least one of: (i) energy efficiency, (ii) air quality, (iii) temperature, (iv) calories, (iv) a motion sensor, (v) a user location within a residence, (vi) multiple users, (vii) a window shade, (viii) a heating or cooling medium, (ix) an entertainment medium, (x) a pet monitoring medium, (xi) a child monitoring medium, (xii) a pool monitoring medium, and (xiii) a water monitoring medium.

25. The medium of claim 19, wherein the lighting parameter is associated with at least one of: (i) a luminescence, (ii) a wattage, (iii) a color characteristic, (iv) a correlated color temperature, and (v) a wavelength.

* * * * *